US005347586A

United States Patent [19]

Hill et al.

[11] Patent Number: 5,347,586

[45] Date of Patent: Sep. 13, 1994

[54] ADAPTIVE SYSTEM FOR CONTROLLING NOISE GENERATED BY OR EMANATING FROM A PRIMARY NOISE SOURCE

[75] Inventors: Peter D. Hill, Monroeville; Thomas H. Putman, Penn Hills Township, Allegheny County, both of Pa.

[73] Assignee: Westinghouse Electric Corporation, Pittsburgh, Pa.

[21] Appl. No.: 874,898

[22] Filed: Apr. 28, 1992

[51] Int. Cl.[5] ...................... A61F 11/06; H03B 29/00

[52] U.S. Cl. ...................... 381/71

[58] Field of Search ...................... 381/71, 94

[56] References Cited

U.S. PATENT DOCUMENTS

| | | | |
|---|---|---|---|
| 4,044,203 | 8/1977 | Swinbanks . | |
| 4,480,333 | 10/1984 | Ross | 381/71 |
| 4,589,133 | 5/1986 | Swinbanks | 381/71 |
| 4,596,033 | 6/1986 | Swinbanks | 381/71 |
| 4,637,048 | 1/1987 | Swinbanks | 381/71 |
| 4,665,549 | 5/1987 | Eriksson et al. | 381/71 |
| 4,677,676 | 6/1987 | Eriksson | 381/71 |
| 4,677,677 | 6/1987 | Eriksson | 381/71 |
| 4,783,818 | 11/1988 | Graupe et al. | 381/71 |
| 4,956,867 | 9/1990 | Zurek et al. | 381/94 |
| 5,018,202 | 5/1991 | Takahashi et al. | 381/71 |
| 5,091,953 | 2/1992 | Tretter | 381/71 |
| 5,224,168 | 6/1993 | Martinez et al. | 381/71 |

OTHER PUBLICATIONS

Elliott et al., "A Multiple Error LMS Algorithm and Its Application to the Active Control of Sound and Vibration," IEEE Transactions on Acoustics, Speech, and Signal Processing, vol. ASSP-35, No. 10, pp. 1423-1434, Oct. 1987.

M. A. Swinbanks, "The Active Control of Low Frequency Sound in a Gas Turbine Compressor installation," Inter-Noise, pp. 423-426, May 17-19, 1982.

Eriksson, et al., "The Selection and Application of an IIR Adaptive Filter for Use in Active Sound Attenuation," IEEE Transactions on Acoustic, Speech, and Signal Processing, vol. ASSP-35, No. 4, pp. 433-437 Apr., 1987.

Eriksson et al., "The Use of Active Noise Control Industrial Fan Noise," ASME Journal, Chicago, Ill., pp. 1-7, Nov. 27-Dec. 2, 1988.

Eriksson et al., "Active Noise Control on Systems with Time-Varying Sources and Parameters," Journal of Sound and Vibration, pp. 16-21, Jul. 1989.

C. F. Ross, "An Adaptive digital Filter for Broadband Active Sound Control," Journal of Sound and Vibration (1982)80(3), 381-388.

A. Roure, "Self-Adaptive Broadband Active Sound Control System," Journal of Sound and Vibration (1985) 101(3), 429-441.

Eriksson, et al., "Active Noise Control and Specifications for Fan Noise Problems," Noise-Con 88, Jun. 20-22, 1988.

*Primary Examiner*—Curtis Kuntz
*Assistant Examiner*—Ping W. Lee
*Attorney, Agent, or Firm*—M. G. Panian

[57] ABSTRACT

An adaptive noise control system comprises a reference microphone (12) (FIG. 2) for generating a reference signal (x(t)) that is correlated with noise emanating from a primary noise source (10), secondary loud speaker sources ($S_1$, $S_2$, . . . $S_N$) for generating a plurality of secondary sound waves, microphones ($e_1$, $e_2$, . . . $e_M$) for detecting a plurality of far-field sound waves in a far-field of the primary noise source and generating a plurality of error signals ($e_1(t)$, $e_2(t)$, . . . $e_M(t)$) each of which is indicative of the power of a corresponding far-field sound wave, and an adaptive controller (14) for controlling the secondary sources in accordance with the reference signal and the error signals so as to minimize the power in the far-field sound waves.

15 Claims, 3 Drawing Sheets

ADAPTIVE SYSTEM FOR CONTROLLING NOISE GENERATED BY OR EMANATING FROM A PRIMARY NOISE SOURCE

FIELD OF THE INVENTION

The present invention generally relates to the field of noise control and more particularly relates to adaptive, active noise control systems. One preferred application of the invention is to control noise in a power generation plant.

BACKGROUND OF THE INVENTION

Free-field noise sources, such as internal combustion engines and combustion turbines, generate powerful low-frequency noise in the 31 Hz and 63 Hz octave bands (where the 31 Hz octave band extends from 22 Hz to 44 Hz and the 63 Hz octave band extends from 44 Hz to 88 Hz). Passive noise control requires the use of large, expensive silencers to absorb and block the noise. The size and cost of such silencers makes passive control unacceptable for many applications. An alternative to passive control is a combination of passive control and active control. Passive control abates noise better as the frequency of the noise increases and active control works better as the frequency of the noise decreases. Therefore a combination of passive and active control may advantageously be employed in many applications.

The active control of sound or vibration involves the introduction of a number of controlled "secondary" sources driven such that the field of acoustic waves generated by these sources destructively interferes with the field generated by the original "primary" source. The extent to which such destructive interference is possible depends on the geometric arrangement of the primary and secondary sources and on the spectrum of the field produced by the primary source. Considerable cancellation of the primary field can be achieved if the primary and secondary sources are positioned within a half-wavelength of each other at the frequency of interest.

One form of primary field that is of particular practical importance is that produced by rotating or reciprocating machines. The waveform of the primary field generated by these machines is nearly periodic and, since it is generally possible to directly observe the action of the machine producing the original disturbance, the fundamental frequency of the excitation is generally known. Each secondary source can therefore be driven at a harmonic of the fundamental frequency by a controller that adjusts the amplitude and phase of a reference signal and uses the resulting "filtered" reference signal to drive the secondary source. In addition, it is often desirable to make this controller adaptive, since the frequency and/or spatial distribution of the primary field may change with time and the controller must track this change.

To construct a practical adaptive controller, a measurable error parameter must be defined and the controller must be capable of minimizing this parameter. One error parameter that can be directly measured is the sum of the squares of the outputs of a number of sensors. The signal processing problem in a system employing such an error parameter is to design an adaptive algorithm to minimize the sum of the squares of a number of sensor outputs by adjusting the magnitude and phases of the sinusoidal inputs to a number of secondary sources. S. J. Elliot et al., in "A Multiple Error LMS Algorithm and Its Application to Active Control of Sound and Vibration," IEEE Trans. on Acoustics, Speech and Signal Processing, Vol. ASSP-35, No. 10, October 1987, describe a least-mean-squares (LMS) based active noise control system, however that system converges too slowly for many applications.

The present invention is directed to systems for controlling both random and periodic noise in a single or multiple mode acoustic environment. (In a multiple mode acoustic environment the amplitude of the sound varies in a plane perpendicular to the direction in which the sound propagates.) There are known systems for controlling random noise propagating in a single mode through a duct, however these systems do not work with multiple mode propagation. See U.S. Pat. Nos. 4,044,203, 4,637,048 and 4,665,549 and M. A. Swinbanks, "The Active Control of Low Frequency Sound in a Gas Turbine Compressor Installation." Inter-Noise 1982, San Francisco, Calif. May 17–19, 1982. pp. 423-427.

SUMMARY OF THE INVENTION

Accordingly, a primary goal of the present invention is to provide noise control methods and apparatus that can rapidly adapt, or converge, to an optimum state wherein the total noise received by a number of detectors placed in prescribed locations is minimized. Adaptive noise control systems in accordance with the present invention comprise reference means for generating a reference signal that is correlated with noise emanating from a primary noise source, secondary source means for generating a plurality of secondary sound waves, detection means for detecting a plurality of far-field sound waves in a far-field of the primary noise source and generating a plurality of error signals each of which is indicative of the power of a corresponding far-field sound wave, and adaptive control means for controlling the secondary source means in accordance with the reference signal and the error signals so as to minimize the power in the far-field sound waves.

In preferred embodiments of the invention, the reference means comprises means for detecting acoustic noise in the near-field of the primary noise source, the secondary source means comprises a plurality of loud speakers, and the detection means comprises a plurality of microphones.

The adaptive control means in preferred embodiments comprises: (i) correlation means for generating autocorrelation data on the basis of the reference signal and generating crosscorrelation data on the basis of the reference signal and the error signals, (ii) FFT means for generating auto-spectrum data and cross-spectrum data on the basis of the autocorrelation and crosscorrelation data, (iii) FIR means for filtering the reference signal in accordance with a plurality of weighting functions and for providing filtered versions of the reference signal to control the output of the secondary source means, each weighting function being associated with a corresponding one of the secondary sound waves to be generated by the secondary source means, and (iv) adapting means for processing the auto-spectrum and cross-spectrum data so as to derive the weighting functions and for providing the weighting functions to the FIR filter means.

Systems in accordance with the present invention may also advantageously comprise random number means for generating substantially random numbers and means for switching the input of the FIR means to the random number means. This enables the performance of a system identification function (described below) in accordance with the invention.

The adapting means may comprise means for performing an inverse Fast Fourier Transformation of the said weighting functions prior to providing them to the FIR filter means.

The present invention may advantageously be applied in a power generation system comprising a combustion turbine coupled to an exhaust stack. In such an application, an adaptive, active control system for controlling multi-mode acoustic noise generated by the combustion turbine and emanating from the exhaust stack comprises reference means for generating a reference signal that is correlated with noise generated by the combustion turbine, secondary source means for generating a plurality of secondary sound waves, detection means for detecting a plurality of far-field sound waves in a far-field of the exhaust stack and generating a plurality of error signals each of which is indicative of the power of a corresponding far-field sound wave, and adaptive control means for controlling the secondary source means in accordance with the reference and error signals so as to minimize the power in the far-field sound waves.

The present invention also encompasses methods comprising steps corresponding to the respective functions of the elements described above.

Noise control methods in accordance with the present invention can theoretically (i.e., under the right conditions) converge in one iteration. Moreover, systems in accordance with the invention are capable of efficiently achieving a large reduction in multi-mode noise, even in non-static noise environments. Other features and advantages of the invention are described below.

DETAILED DESCRIPTION OF PREFERRED EMBODIMENTS

The theory underlying the present invention will now be described with reference to FIG. 1, which depicts a primary noise source NS surrounded by N secondary noise sources (or control sources) $S_1$–$S_N$, where N represents an integer. The primary noise source NS may be composed of one or more sources that radiate sound waves. Error microphones $e_1$–$e_M$, where M represents a number greater than or equal to the number of secondary sources N, detect sound waves in the far-field (approximately 150 ft. (45 meters)) of the primary noise source NS and provide feedback to a control system (not shown) that controls the secondary noise sources $S_1$–$S_N$ such that the total noise received by the error microphones is reduced. The secondary sources are driven by the output of a filter (not shown), which is part of the control system. The input to the filter, called the reference, may be derived by sampling the sound in the near-field of the primary noise source NS (e.g., within a few feet of NS). Alternatively, if the primary noise is periodic, a synchronization signal of a prescribed frequency may be used to generate the reference. Using current technology, the control system's filter can most easily be implemented with a digital signal processor. The following analysis is therefore in the discrete time and "z" domains. (Those skilled in this art will recognize that the z domain is reached by performing a z-transform of sampled, or discrete time, data. The z-transformation of sampled data between the discrete time and z domains is analogous to the Laplace transformation of mathematical functions between the time and frequency domains. The z-transform is a superclass of the discrete Fourier transform.)

Figure 1:
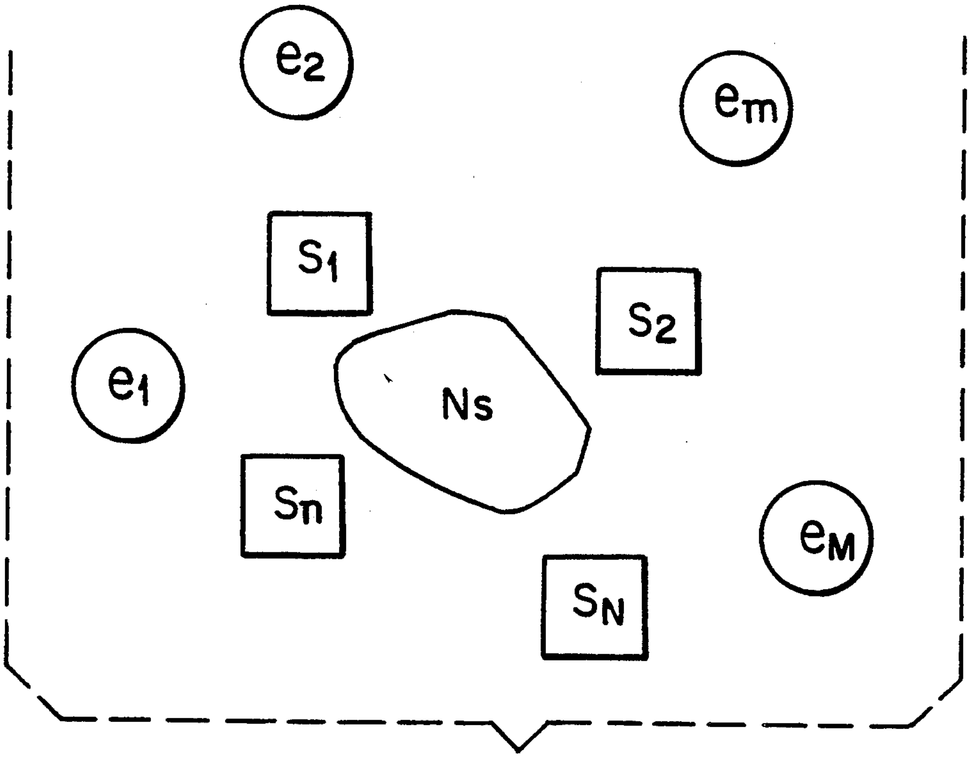
FIG. 1 is a schematic representation of a noise control system in accordance with the present invention.

Referring to FIG. 1, an error microphone $e_m$ (where m represents any number between 1 and M) receives sound from the primary noise source NS and the secondary sources $S_1$ to $S_N$. The sound generated by NS and detected by error microphone $e_m$ is represented as $d_m$ in this analysis. Thus $e_m(z)$ is given by the following equation:

$$e_m(z) = d_m(z) + \sum_{n=1}^{N} y_{mn}(z)S_n(z) \quad (1)$$

Since there are M error microphones, the following matrix equation is formed:

$$E] = D] + [Y]S] \quad (2)$$

where, $$E] = [e_1(z), e_2(z), \ldots e_m(z), \ldots e_M(z)]^T$$

$$D] = [d_1(z), d_2(z), \ldots d_m(z), \ldots d_M(z)]^T$$

$$[Y] = [Y_{mn}(z)]$$

$$S] = [S_1(z), S_2(z), \ldots S_n(z), \ldots S_N(z)]^T$$

The element $Y_{mn}$ of the Y matrix represents the transfer function where the control signal $S_n(z)$ is the input to secondary source $S_n$ and the signal $e_m(z)$ is the output of error microphone $e_m$; i.e., $Y_{mn} = e_m(z)/S_n(z)$ with $S_1(z), \ldots S_{n-1}(z), S_{n+1}(z), \ldots S_N(z) = 0$.

As mentioned above, the control signal $S_n(z)$ is the input to secondary source $S_n$, however it is also the output of the control system's digital filter (described below) with the input to the filter being a reference signal X(z). $S_n(z)$ may be determined from X(z), a filter function $W_n(z)$ and the following equation:

$$S_n(z) = W_n(z)X(z) \quad (3)$$

Substituting equation (3) into equation (2) yields:

$$E] = D] + [Y]W]X(z) \quad (4)$$

where, $$W] = [W_1(z), W_2(z), \ldots W_N(z)]^T \quad (5)$$

The least squares solution to equation (4) (i.e., the values of W] that minimize the total noise power in E], given by $e_1^2(z) + e_2^2(z) + \ldots e_M^2(z)$) is $$W] = -([Y]^H[Y])^{-1}[Y]^H X^*(z)D]/X^*(z)X(z) \quad (6)$$

where, $[Y]^H$ represents the conjugate transpose, or Hermitian, of [Y], and $X^*(z)$ represents the conjugate of X(z). In equation (6), the product $X^*(z)D]$ is the cross-spectrum of the reference X(z) and the noise matrix D]. The auto-spectrum $X^*(z)X(z)$ is a complex number and is divided into the cross-spectrum $X^*(z)D]$. (Note that the cross- and auto-spectrums are also referred to in this specification as "$G_{xx}(z)$" and "$G_{xem}(z)$", respectively.)

The least-squares solution of W] can be found in one iteration with equation (6), provided there are no measurement errors in [Y], D] or X(z). In practice, however, errors in [Y], D] and X(z) are significant enough to require the following iterative solution:

$$W] = W] - \mu([Y]^H[Y]^{-1}[Y]^H X^*(z)E]/X^*(z)X(z) \tag{7}$$

where $\mu$ is a convergence factor. If $\mu=1$, equation (7) will reduce to equation (6) because E]=D] when W]=0]. Typical values of $\mu$ are in the range of 0.1 to 0.5.

Both the cross-spectrum $X^*E]$ and auto-spectrum $X^*X$ can be computed by taking the discrete Fourier transform, implemented, e.g., by the Fast Fourier Transform (FFT), of the crosscorrelation of x(t) and $e_m(t)$ and autocorrelation of x(t), respectively (where x(t) represents the time-domain version of X(z)). The autocorrelation of x(t), designated $R_{xx}(t)$, and crosscorrelation of x(t) and $e_m(t)$, designated $R_{xem}(t)$, are given by the following equations:

$$R_{xx}(t) = \frac{1}{L}\sum_{k=0}^{L-1} x(k)x(k-t) \tag{8}$$

$$R_{xem}(t) = \frac{1}{L}\sum_{k=0}^{L-1} e_m(k)x(k-t) \tag{9}$$

where, k is the discrete time index, x(k) represents the reference signal in the discrete time-domain, $e_m(k)$ represents the error signal, in the discrete time-domain, from error microphone number m, and L represents the number of samples used to compute $R_{xx}(t)$ and $R_{xem}(t)$ (note that the accuracy of the computation may be increased by increasing the number of samples L, however the disadvantage of making L unnecessarily large is that the frequency at which the filters can be updated is inversely proportional to L).

To properly transform $R_{xx}(t)$ and $R_{xem}(t)$ into the frequency domain (i.e., the z-domain), the H-point vectors must be padded with zeros such that the resulting vector is 2H points long:

$$R_{xx}(t) = [R_{xx}(0), R_{xx}(1), \ldots R_{xx}(h), \ldots R_{xx}(H-1), \underbrace{0, \ldots 0]}_{H\ \text{zeros}}$$

$R_{xx}(t)$ is then transformed to the auto-spectrum $G_{xx}(z)$ with a 2H-point FFT. $R_{xem}(t)$ is transformed in the same manner to $G_{xem}(z)$.

Due to causality constraints, the $W_n(z)$ weighting functions must be transformed to the time-domain. The control signal $s_n(t)$ is computed from $$S_n(k) = \sum_{t=0}^{H-1} w_n(t)x(k-t) \tag{10}$$

where $w_n(t)$ represents the time-domain versions of the filter functions $W_n(z)$ and H represents the length of the filter functions $W_n(t)$ (also referred to as the number of taps in the respective filters). A 2H-point inverse discrete Fourier transform may be used to convert $W_n(z)$ to $W_n(t)$. Only the first H points of the result are used in equation (10).

An application of the present invention to the suppression of noise emanating from the exhaust stack of a combustion turbine will now be described with reference to FIGS. 2 and 3. The dimensions of the cross-section of the stack are assumed to be greater than the wavelengths of the sound waves that emanate therefrom, therefore multi-mode noise will be generated.

Figure 2:
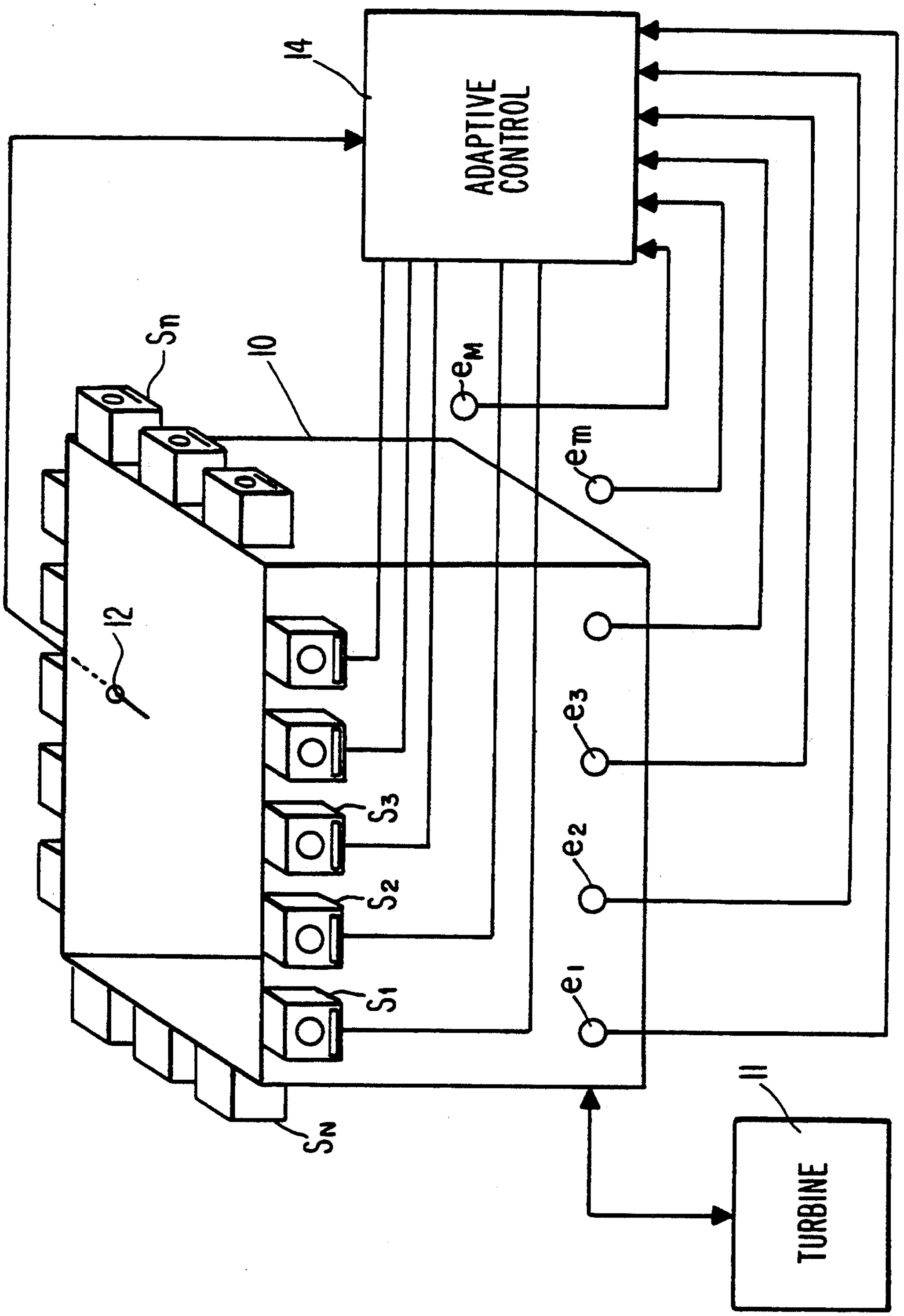
FIG. 2 depicts a noise control system in accordance with the present invention in the context of a power generation system.

FIG. 2 depicts a power generation system employing an active, adaptive noise control system in accordance with the present invention. In this system, a plurality of loudspeakers $S_1$–$S_N$ are positioned around the top rim of an exhaust stack 10 of a combustion turbine 11. A reference signal x(t) is measured by a probe microphone 12 in the stack 10. A plurality of error microphones $e_1$–$e_M$ (with M>=N) are located in the far-field of the exhaust stack. An adaptive control system 14 takes feedback from the error microphones $e_1$–$e_M$ and the reference signal x(t) from the probe microphone 12 and drives the loudspeakers $S_1$–$S_N$ so as to substantially cancel the noise detected by the error microphones.

Figure 3:
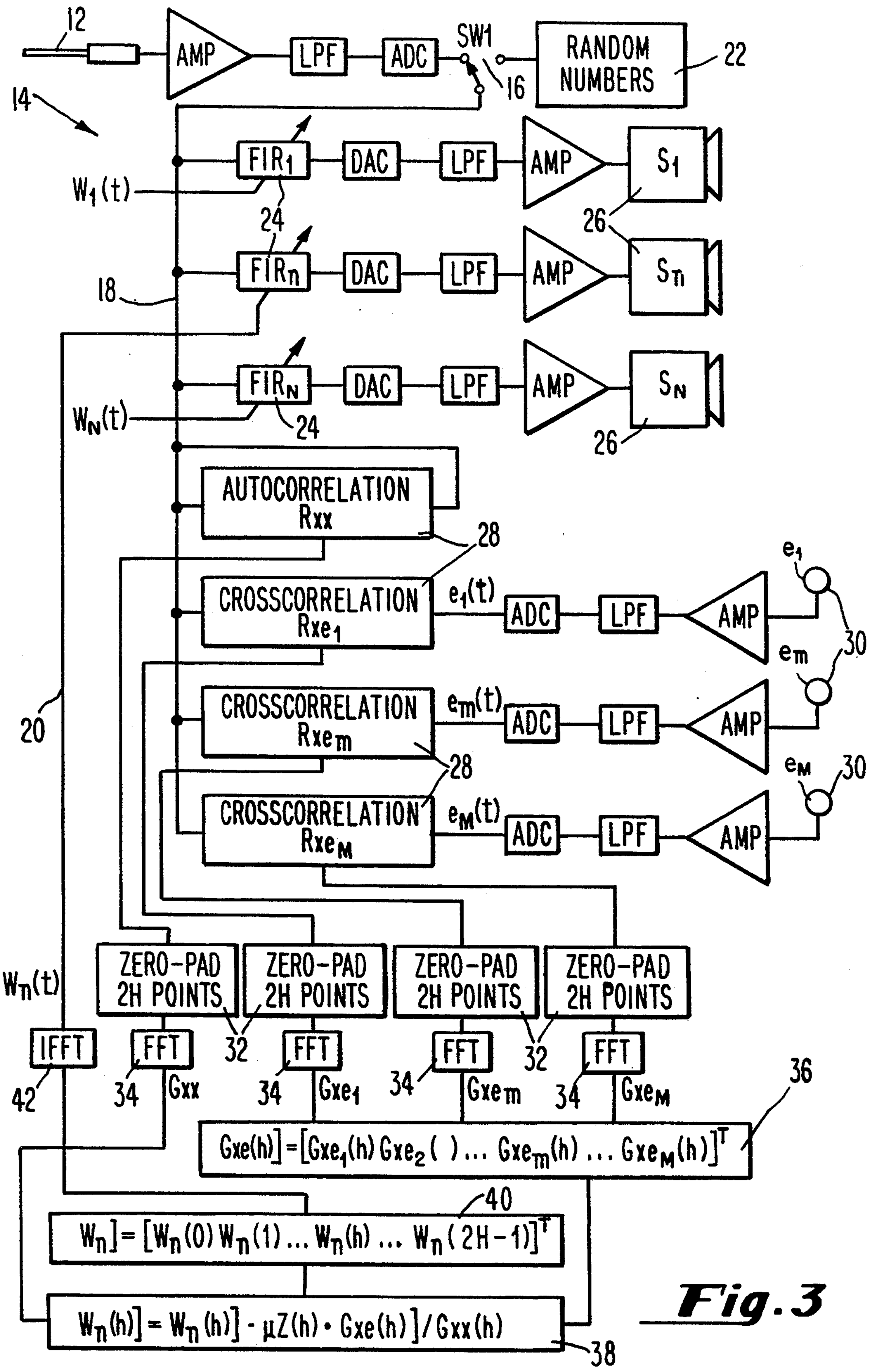
FIG. 3 is a more detailed block diagram of the noise control system of FIG. 1, with emphasis on the adaptive control block 14.

FIG. 3 is a more detailed block diagram of the system of FIG. 2, with emphasis given to the adaptive control system 14. (The turbine 11 and exhaust stack 10 are not shown in FIG. 3.) The reference numerals 12–42 refer to both structural elements (or hardware) and functional elements that may be implemented with hardware in combination with software; although the respective functional elements are depicted as separate blocks, it is understood that in practice more than one function may be performed by a given hardware element.

The reference numerals are used as follows: 12-probe microphone, 14-adaptive control system, 16-switch, 18-bus, 20-bus, 22-random number generator, 24-finite impulse response filters $FIR_i$–$FIR_N$, 26-secondary source loud speakers $S_1$–$S_N$, 28-auto/cross-correlation blocks, 30-error detector microphones, 32-zero-pad blocks, 34-Fast Fourier Transform (FFT) blocks, 36-cross-spectrum array, 38-processing block, 40-processing block, and 42-inverse Fast Fourier Transform (IFFT) block. In one embodiment of the present invention, there are three processors (two digital signal processors and one microprocessor) involved in (1) filtering the reference and generating the secondary source signals $S_1(t)$–$S_N(t)$ (which drive the respective loudspeakers $S_1$–$S_N$), (2) receiving the error signals and computing the autocorrelation and crosscorrelation vectors $R_{xx}(t)$, $R_{xe1}(t)$–$R_{xeM}(t)$, and (3) carrying out the FFTs, updating the filter coefficients and carrying out the inverse FFT.

One problem encountered by the present inventors is the causality of the reference signal with respect to the sound at the secondary sources. The group delay characteristics of the low-pass filters (LPFs), the high-pass response of the secondary sources $S_1$–$S_N$, and the delay of the digital filters $FIR_1$–$FIR_N$ must be less than the time that the noise takes to travel from the probe microphone 12 to the closest secondary source. Therefore, to derive each control signal $s_n(t)$ the reference signal x(t) is filtered in the time domain with a finite impulse response (FIR) filter. It has been argued that the filters are best implemented by an infinite impulse response (IIR) filter. See L. J. Eriksson, et al., "The Selection and Application of an IIR Adaptive Filter for Use in Active Sound Attenuation," IEEE Trans. on Acoustics, Speech and Signal Processing, Vol. ASSP-35, No. 4, April, 1987, pp. 433–437 and L. J. Eriksson, et al., "The Use of Active Noise Control for Industrial Fan Noise," American Society of Mechanical Engineers Winter Annual Meeting, Nov. 27—Dec. 2, 1988, 88-WA/NCA-4. However, because of the potential instability of IIR filters, the present invention employs intrinsically stable FIR filters, with the understanding that a large number of filter taps may be required in particular applications.

Another problem encountered by the inventors is the updating of the filter coefficients $W_n(t)$ of the FIR filters. Typically, adaptive filters implemented in the time-domain are updated in accordance with time-domain algorithms. Elliot describes such a system in S. J. Elliot, et al., "A Multiple Error LMS Algorithm and Its Application to Active Control of Sound and Vibration, " IEEE Trans on Acoustics, Speech and Signal Processing, Vol. ASSP-35, No. 10, October 1987. However, the convergence time of an LMS-based control system (i.e., the time that the control system 14 needs to adjust the filter coefficients to optimum values) can be many orders of magnitude greater than the convergence time of the present invention, which adjusts the filter coefficients in the frequency domain.

Frequency domain adaptive algorithms have very advantageous properties, such as orthogonal reference signal values, which are a direct result of taking the FFT of the autocorrelation of x(t) (i.e., the frequency components of $G_{xx}(z)$ are independent of one another). In addition, the entire updating process is decomposed into harmonics, or frequency "bins", which makes the process easier to understand, and thus control, than a time-domain process. In preferred embodiments of the present invention, the filter functions $W_1(z)$–$W_N(z)$ are generated in the frequency domain and then converted to the time-domain functions $w_1(t)$–$w_N(t)$. The time-domain functions $w_1(t)$–$w_N(t)$ are provided via a set of busses 20 (only one bus 20 is shown in FIG. 3) to the FIR filters $FIR_1$–$FIR_N$.

The adaptive control system 14 must first identify the system before optimizing the FIR filters. System identification involves determining the respective transfer functions $y_{mn}(t)$ from the inputs of the digital-to-analog convertors (DACs) (FIG. 3), through the speakers $S_n$, the acoustic path from the speakers $S_n$ to the error microphone $e_m$, and finally to the outputs of the analog-to-digital convertor (ADCs). This is accomplished by generating random numbers with a digital random number generator 22 and outputting these numbers via a switch 16 to a bus 18 coupled to the respective FIR filters and to inputs of autocorrelation and crosscorrelation blocks, which compute autocorrelation and cross-correlation data. As a final step, the auto- and crosscorrelation data ($R_{xx}(t)$ and $R_{xe1}(t)$–$R_{xeM}(t)$) is converted to 2H-point frequency-domain data ($G_{xx}(z)$ and $G_{xe1}(z)$–$G_{xeM}(z)$) by zero-pad and FFT blocks 32, 34.

System Identification

The system identification process may be summarized as follows:

Step 1: Set switch 16 to the random number generator 22.

Step 2: Set $n=1$

Step 3: Zero all FIR coefficients $W_n(h)$ (for $h=1$ to $2H-1$) and set $W_n(0)$ to 1.0.

Step 4: Compute autocorrelation and crosscorrelation data using equations (8) and (9).

Step 5: Zero pad $R_{xx}(t)$ and $R_{xe1}(t)$–$R_{xeM}(t)$ and take the FFT of each to produce $G_{xx}(h)$ and $G_{xe1}(h)$–$G_{xeM}(h)$, where h now represents the harmonic index of the FFT and takes values from 0 to $2H-1$. (Note that the actual frequency corresponding to the index h is a function of the sampling frequency and the number of points 2H, and may be determined by well-known techniques.)

Step 6: Compute $Y_{mn}(h)$ using the following formula:

$$Y_{mn}(h)=G_{xem}(h)/G_{xx}(h) \quad (11)$$

for $h=0$ to $H-1$ and $m=1$ to M.

Step 7: If n is not equal to N (the number of secondary sources), increment n by 1 and repeat steps 3 through 6.

Step 8: Compute the Z matrix for each harmonic h as follows:

If $N=M$, compute Z as follows:

For $h=0$ to $H-1$ do $$[Z_{mn}(h)]=[Y_{mn}(h)]^{-1} \quad (12)$$

If $M>N$, compute Z as follows:

For $h=0$ to $H-1$ do $$[Z_{mn}(h)]=[Y_{mn}(h)]^H[Y(h)]^{-1}[Y(h)]^H \quad (13)$$

(Note that the superscript H in equation (13) represents the Hermitian operator.)

Adaptation

Adaptation determines the optimum filter coefficients for each FIR filter. The adaptation process may be summarized as follows:

Step 1: Set switch 16 (FIG. 3) to the ADC of the reference channel coupled to the probe microphone 12.

Step 2: Zero all FIR coefficients $w_n(t)$ and $W_n(z)$ for $n=1$ to N.

Step 3: Compute autocorrelation and crosscorrelation data using equations (8) and (9).

Step 4: Zero pad $R_{xx}(t)$ and $R_{xe1}(t)$ –$R_{xeM}(t)$ to 2H points and take the FFT of each to produce $G_{xx}(h)$ and $G_{xe1}(h)$–$G_{xeM}(h)$; set $n=1$.

Step 5: Compute frequency-domain filter coefficients $W_n(h)]$using $$W_n(h)]=W_n(h)]-\mu[Z(h)]G_{xe}(h)]/(G_{xx}^*(h)G_{xx}(h)) \quad (14)$$

where $h=0$ to $2H-1$.

Step 6: Inverse discrete Fourier transform $W_n(h)]$ into the time-domain coefficients $w_n(t)]$.

Step 7: Load updated time-domain coefficients $w_n(t)$ into filter $FIR_n$.

Step 8: If n is not equal to N (the number of secondary sources), increment n by 1 and repeat steps 5 through 7.

Necessary Conditions for Active Control

The following conditions must be met for active control to successfully reduce random noise (these are designated the "four C's"):

1) There must be sufficient coherence between the reference microphone signal and the far-field sound pressure.
2) If there are multiple noise sources, they must have coalesced and appear as one source.
3) Sampling of the reference signal must be sufficiently advanced in time to compensate for the transient response of the active control system. This is called the causality requirement.
4) The secondary control sources must have sufficient capacity to generate a cancelling sound field.

Each of these requirements are briefly discussed below.

Coherence

The coherence between two signals ranges from 0 to 100 percent. In the case of the exhaust stack 10, the reference microphone 12 detects the sound inside the stack and, barring any other noise sources, this sound should be highly related to, or coherent with, the sound at the top of the stack and the sound detected by the far-field microphones $e_1$–$e_M$. In other words, the sound power detected by the far-field microphones should nearly be 100% the result of the sound radiating from the top of the exhaust stack 10. In reality, however, the percentage of the sound power detected by the far-field microphones that comes from the top of the stack drops as the sound generated by other unrelated noise sources (such as a mechanical package, turbine inlet and turbine housing) is detected. For example, if the coherence between the sound at the top of the stack 10 and the sound detected by the far-field microphones $e_1$–$e_M$ is 60%, then 40% of the sound power detected in the far-field will be related to other noise sources, such as the turbine housing and mechanical package. To illustrate the importance of coherence in assessing the value of a given noise control system, suppose that all of the noise radiating from the exhaust stack were eliminated. Then the sound power in the far-field would decrease by 60%, or 4 dB.

The following table lists the theoretical maximum noise reduction for a given coherence between the reference signal x(t) and the far-field signals.

| COHERENCE | NOISE REDUCTION POWER RATIO |
|---|---|
| 100% | Infinite |
| 99% | 20 dB |
| 90% | 10 dB |
| 80% | 7 dB |
| 60% | 4 dB |
| 50% | 3 dB |

Coalescence

The combustion chambers of a combustion turbine can be considered distinct and mutually incoherent noise sources. The sound emanating from each of the combustion chambers mixes, or coalesces, as it propagates through the exhaust section and into the exhaust stack. Once the noise has coalesced in the exhaust stack, the sound at any location in the stack should be more than 90% coherent with the sound at any other location in the stack. However, turbulence noise produced, e.g., by the flow of exhaust gases through the plenum and silencer creates spatially incoherent noise in the exhaust stack and thus the coherence between the sound at two points in the stack will decrease as the distance between the two points increases. Turbulence noise generated by flow through a silencer is often called self noise. If the exhaust flow is turbulence-free after the exhaust silencer, the spatially incoherent sound at the exhaust silencer will coalesce once again as it propagates up the exhaust stack.

Causality

Causality refers to the requirement that the reference signal x(t) must be obtained a sufficient amount of time before the sound reaches the control speakers $S_1$–$S_N$ for the control system 14 to filter the reference signal and drive the speakers. The transient delay of one embodiment of the have a transient delay of about 12 ms. Therefore the total time delay from the reference microphone input to the acoustic output of the speakers is about 15 ms. Since sound travels about 1 foot per 1 ms, the reference microphone should be approximately 15 ft (4.6 meters) from the top of the stack. A shorter distance may produce satisfactory results for some applications.

Capacity (or Control Power)

The loudspeakers $S_1$–$S_N$ should be able to generate as much sound power as that emanating from the stack 10. However, because of the interaction between independent control sources, the specified power levels for the loudspeakers should be at least twice that radiated by the exhaust stack.

Experimental Results

A three speaker (i.e., three secondary sources) and four error microphone active control system in accordance with the present invention has been tested. A low-pass-filtered (0–100 Hz) random signal acted as the driving signal to a primary noise source speaker and as the reference signal x(t). The filter coefficient optimization process was frequency-limited by the operator to 20–170 Hz. Reductions in sound pressure level (SPL) of up to 27 dB were achieved between 20 Hz to 120 Hz. A slight increase in SPL was noted between 120 Hz and 160 Hz. This problem was solved by setting the upper frequency limit to 120 Hz.

We claim:

1. An adaptive system for controlling noise generated by or emanating from a primary noise source, comprising:

(a) reference means for generating a reference signal (x(t)) that is correlated with the noise emanating from the primary noise source;

(b) secondary source means for generating a plurality of secondary sound waves;

(c) detection means for detecting a plurality of far-field sound waves in a far-field of said primary noise source, and generating a plurality of error signals each of which is indicative of the power of a corresponding far-field sound wave; and (d) adaptive control means for controlling said secondary source means in accordance with said reference signal and said error signals so as to minimize the power in said far-field sound waves; wherein said adaptive control means comprises:

(i) correlation means for generating autocorrelation data on the basis of said reference signal and generating crosscorrelation data on the basis of said reference signal and said error signals;

(ii) fast Fourier transform (FFT) means for generating auto-spectrum data and cross-spectrum data on the basis of said autocorrelation and crosscorrelation data;

(iii) finite impulse response (FIR) means, coupled to said reference means, for filtering said reference signal in accordance with a plurality of weighting functions and for providing filtered versions of said reference signal to control the output of said secondary source means, each of the weighting functions being associated with a corresponding one of said secondary sound waves to be generated by said secondary source means; and (iv) adapting means for processing said auto-spectrum and cross-spectrum data so as to derive said weighting functions, and for providing said weighting functions to said FIR means.

2. An adaptive system for controlling noise generated by or emanating from a primary noise source, comprising:

(a) reference means for generating a reference signal that is correlated with the noise emanating from the primary noise source;

(b) secondary source means for generating a plurality of secondary sound waves;

(c) detection means for detecting a plurality of far-field sound waves in a far-field of said primary noise source, and generating a plurality of error signals each of which is indicative of the power of a corresponding far-field sound wave; and (d) adaptive control means for controlling said secondary source means in accordance with said reference signal and said error signals so as to minimize the power in said far-field sound waves;

wherein said reference means comprises means for detecting acoustic noise in a near-field of said primary noise source;

wherein said secondary source means comprises a plurality of loudspeakers;

wherein said detection means comprises a plurality of microphones; and wherein said adaptive control means comprises:

(i) correlation means for generating autocorrelation data on the basis of said reference signal and generating crosscorrelation data on the basis of said reference signal and said error signals;

(ii) fast Fourier transform (FFT) means for generating auto-spectrum data and cross-spectrum data on the basis of said autocorrelation and crosscorrelation data;

(iii) finite impulse response (FIR) means, coupled to said reference means, for filtering said reference signal in accordance with a plurality of weighting functions and for providing filtered versions of said reference signal to control the output of said secondary source means, each of the weighting functions being associated with a corresponding one of said secondary sound waves to be generated by said secondary source means; and (iv) adapting means for processing said auto-spectrum cross-spectrum data so as to derive said weighting functions, and for providing said weighting functions to said FIR means.

3. The system described in claim 2, further comprising random number means for generating substantially random numbers and means for switching the input of said FIR means to said random number means, wherein a system identification function is performed.

4. The system described in claim 3, wherein said adapting means comprises inverse FFT means for performing an inverse Fast Fourier Transformation of said weighting functions prior to providing them to said FIR means.

5. A power generation system, comprising a combustion turbine coupled to an exhaust stack, and an adaptive, active control system for controlling multi-mode acoustic noise generated by said combustion turbine and emanating from said exhaust stack, said active control system comprising:

(a) reference means for generating a reference signal that is correlated with the noise generated by said combustion turbine;

(b) secondary source means for generating a plurality of secondary sound waves;

(c) detection means for detecting a plurality of far-field sound waves in a far-field of said exhaust stack, and generating a plurality of error signals each of which is indicative of the power of a corresponding far-field sound wave; and (d) adaptive control means for controlling said secondary source means in accordance with said reference signal and said error signals so as to minimize the power in said far-field sound waves, said adaptive control means comprising:

(i) correlation means for generating autocorrelation data on the basis of said reference signal and generating crosscorrelation data on the basis of said reference signal and said error signals;

(ii) Fast Fourier Transform (FFT) means for generating auto-spectrum data and cross-spectrum data on the basis of said autocorrelation and crosscorrelation data;

(iii) finite impulse response (FIR) means, coupled to said reference means, for filtering said reference signal in accordance with a plurality of weighting functions and for providing filtered versions of said reference signal to control the output of said secondary source means, each of the weighting functions being associated with a corresponding one of said secondary sound waves to be generated by said secondary source means; and (iv) adapting means for processing said auto-spectrum and cross-spectrum data so as to derive said weighting functions, and for providing said weighting functions to said FIR means.

6. A power generation system as described in claim 5, wherein said reference means comprises means for detecting acoustic noise in a near-field of said exhaust stack.

7. A power generation system as described in claim 6, wherein said secondary source means comprises a plurality of loudspeakers.

8. A power generation system as described in claim 7, wherein said detection means comprises a plurality of microphones disposed in the far-field of said exhaust stack.

9. A power generation system as described in claim 8, further comprising random number means for generating substantially random numbers and means for switching the input of said FIR means to said random number means, wherein a system identification function is performed.

10. A power generation system as described in claim 9, wherein said adapting means further comprises inverse FFT means for performing an inverse Fast Fourier Transformation of said weighting functions prior to providing them to said FIR means.

11. A method for controlling noise emanating from a primary noise source, comprising the steps of:

(a) generating a reference signal that is correlated with the noise emanating from said primary noise source;

(b) generating a plurality of secondary sound waves in a near-field of said primary noise source;

(c) detecting a plurality of far-field sound waves in a far-field of said primary noise source, and generating a plurality of error signals each of which is indicative of the power of a corresponding far-field sound wave; and (d) controlling the generation of said secondary sound waves in accordance with said reference signal and said error signals so as to minimize the power in said far-field sound waves, said controlling step including the following sub-steps:

(i) generating autocorrelation data on the basis of said reference signal and generating crosscorrelation data on the basis of said reference signal and said error signals;

(ii) generating auto-spectrum data and cross-spectrum data on the basis of said autocorrelation and crosscorrelation data;

(iii) processing said auto-spectrum and cross-spectrum data so as to derive a plurality of weighting functions; and (iv) filtering said reference signal in accordance with said weighting functions, and employing filtered versions of said reference signal to control the generation of said secondary sound waves, each of the weighting functions being associated with a corresponding one of said secondary sound waves to be generated.

12. A method as described in claim 11, wherein step (a) comprises detecting acoustic noise in the near-field of said primary noise source.

13. A method as described in claim 12, wherein step (b) comprises the excitation of a plurality of loudspeakers.

14. A method as described in claim 13, wherein step (c) comprises the detection of said far-field sound waves with a plurality of microphones disposed in the far-field of said primary noise source.

15. A method as described in claim 14, wherein said adapting step (d)(iv) comprises performing an inverse fast Fourier transformation of said weighting functions.

* * * * *